(12) United States Patent
Bouton et al.

(10) Patent No.: US 7,061,252 B2
(45) Date of Patent: Jun. 13, 2006

(54) ELECTRICAL ARCING PROTECTION CIRCUIT

(75) Inventors: Chad E. Bouton, Delaware, OH (US); Felicia R. Ruggeri, Columbus, OH (US)

(73) Assignee: Hudson Respiratory Care, Inc., Durham, NC (US)

( * ) Notice: Subject to any disclaimer, the term of this patent is extended or adjusted under 35 U.S.C. 154(b) by 0 days.

(21) Appl. No.: 10/884,087

(22) Filed: Jul. 2, 2004

(65) Prior Publication Data

US 2006/0001433 A1 Jan. 5, 2006

(51) Int. Cl.
*G01R 31/08* (2006.01)
*A62B 7/00* (2006.01)
*H05B 3/00* (2006.01)

(52) U.S. Cl. ............. 324/536; 128/203.17; 128/204.17; 219/481; 219/67; 392/398; 392/401

(58) Field of Classification Search ................ 324/536, 324/522, 509; 361/2
See application file for complete search history.

(56) References Cited

U.S. PATENT DOCUMENTS

| 4,682,010 | A |   | 7/1987  | Drapeau et al. ........... 392/488 |
|-----------|---|---|---------|-----------------------------------|
| 5,452,223 | A | * | 9/1995  | Zuercher et al. ............... 702/58 |
| 5,537,996 | A |   | 7/1996  | McPhee .................. 128/204.17 |
| 5,640,951 | A |   | 6/1997  | Huddart et al. ......... 128/204.17 |
| 6,107,611 | A | * | 8/2000  | Jones .......................... 219/509 |
| 6,366,208 | B1| * | 4/2002  | Hopkins et al. ............ 340/650 |
| 6,426,632 | B1| * | 7/2002  | Clunn ......................... 324/509 |
| 6,437,576 | B1| * | 8/2002  | Lorito ........................ 324/509 |
| 6,598,604 | B1| * | 7/2003  | Seakins .................. 128/203.17 |
| 6,667,691 | B1| * | 12/2003 | Sapir ......................... 340/635 |
| 2002/0083947 | A1 |   | 7/2002 | Seakins ................. 128/204.17 |

FOREIGN PATENT DOCUMENTS

WO    WO 86/02566    5/1986

* cited by examiner

*Primary Examiner*—Diane Lee
*Assistant Examiner*—Marina Kramskaya
(74) *Attorney, Agent, or Firm*—Baker & Hostetler LLP

(57) ABSTRACT

A protection circuit, configured to detect and suppress electrical pre-arcing and arcing conditions in a resistive heater wire circuit, comprises a transient voltage suppressor, signal level sensing load coupled to the output of the voltage suppressor, detection and control circuitry, and a high-speed switch or electrical gate. The control circuitry is configured to control the operation of the switch, coupled between said control circuitry and the heater wire, wherein the switch is opened in response to an electrical pre-arcing or arcing condition or a short circuit condition.

35 Claims, 6 Drawing Sheets

ELECTRICAL ARCING PROTECTION CIRCUIT

BACKGROUND OF THE INVENTION

1. Field of the Invention

The present invention relates to a device for preventing or suppressing an electrical pre-arcing condition in a heated respiratory breathing circuit.

2. Description of the Related Art

Ventilator circuits are designed for directing breathing gas supplied by a ventilator or respirator to a patient. Typically, the breathing gas is humidified by a humidifier cooperating with the respiratory circuit, often located at or near the ventilator or respirator whereby the humidified gas travels along a substantial length of the inspiratory limb of the respiratory circuit. The humidified gas becomes cooled as it travels along the inspiratory tubing resulting in condensation or "rain out" inside the tubing. To prevent such condensation, which otherwise could interfere with the efficiency of the breathing circuit and possible injury to a patient, the circuit may be provided with heater wire extending along the interior of the tubing, or embedded in or otherwise secured along the wall of the tubing. Examples of such heated ventilator circuits are described in U.S. Pat. Nos. 4,682,010, 5,537,996, 5,640,951, and international application number WO 86/02566. A single heater wire loop having two ends attached to a plug or connector for supplying electrical current for heating the wire is commonly used.

In respiratory circuits, the breathing air supplied by the ventilator comprises a air mixture having a relatively high concentration of oxygen. It will be understood that because of such high oxygen levels, the gaseous mixture is extremely combustible. Because the heater wire is a resistive wire through which an electrical current passes to accomplish the heating, arcing caused by a short or an open circuit condition may result in ignition and subsequent combustion of the gaseous mixture and possibly causing extremely dangerous fires and injury to a patient.

SUMMARY OF THE INVENTION

The apparatus described herein is directed to an arc prevention/suppression circuit for providing ultra-fast short circuit protection and open circuit protection. The circuit protection apparatus herein is configured to detect, prevent, and suppress electrical arcing and pre-arcing conditions, such as high voltage transients, in a resistive heater wire circuit and to interrupt, terminate or shut off electrical current supplied to the heater wire circuit. The arcing protection circuit removes the ignition energy in the heated respirator circuit and prevents combustion therein.

DETAILED DESCRIPTION OF THE PREFERRED EMBODIMENTS

Embodiments of the invention are described with reference to the accompanying Figures, wherein like numerals refer to like elements throughout. The terminology used in the following description is not intended to be interpreted in any limited or restrictive manner, simply because it is being utilized in conjunction with a detailed description of certain specific embodiments of the invention.

Figure 1:
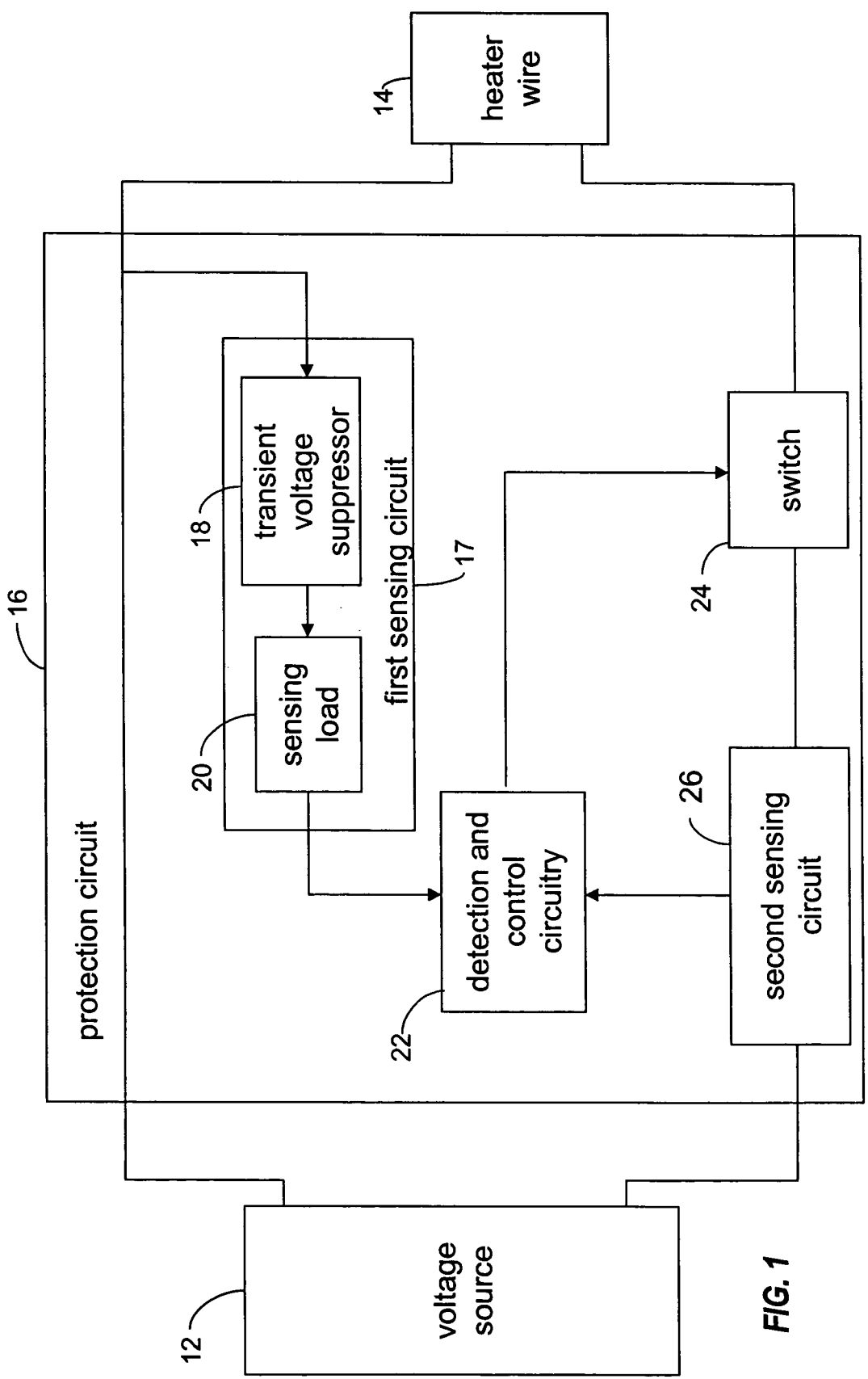
FIG. 1 is a block diagram of one embodiment of a humidifier heater circuit including an electrical arcing protection circuit according to the present invention.

Power is typically supplied to a humidifier heater circuit via a standard AC supply, and a heater wire is supplied with power from the secondary side of a step-down transformer. According to the present invention, a protection circuit configured to detect an arcing condition, or conditions which can lead to arcing in the humidifier heater circuit, is incorporated into the humidifier circuit. In FIG. 1, a block diagram of one embodiment of an electrical arcing protection circuit 16 is illustrated, wherein the protection circuit 16 is coupled between a voltage source 12 and a heater wire 14. The protection circuit 16 is configured to terminate the voltage supplied to and dissipate energy stored in the heater wire 14 in response to detection of a pre-arcing or arcing condition, such as a transient voltage spike, open circuit, or short circuit condition.

As shown in FIG. 1, the protection circuit 16 comprises a first sensing circuit 17, which comprises a transient voltage suppressor 18 and a first sensing load 20. The voltage suppressor 18 is coupled to the voltage source 12 and configured to detect transient voltage spikes. The voltage suppressor 18 can be implemented, for example, with a SIDACtor device. In response to detection of a transient voltage spike the voltage suppressor 18 sinks current through the sensing load 20 to dissipate the excess current due to the voltage spike and obtain a voltage level corresponding to the current level through the voltage suppressor 18. Detection and control circuitry 22 is coupled to the sensing load 20 and configured to open a switch 24, coupled between the control circuitry 22 and the hater wire 14, in response to detection of the voltage level at the sensing load 20 above a predefined voltage level. In one embodiment, the switch 24 is a high-speed switch such as a MOSFET, and is configured to open in less than 100 ns, for example.

The protection circuit 16 further comprises a second sensing circuit 26, coupled to the voltage source 12, the detection and control circuitry 22, and the switch 24. In one embodiment, the second sensing circuit 26 comprises a second sensing load, and the detection and control circuitry 22 is configured to open the switch 24 in response to detecting a level of current through the second sensing load that exceeds a predefined threshold. As will be appreciated by those skilled in the art, each sensing load may comprise a resistor, inductor, or combination thereof, for example.

In one embodiment, the detection and control circuitry 22 comprises at least one comparator configured to output an appropriate signal to open the switch 24 in response to a determination that the voltage at the sensing load 20 exceeds a predefined voltage level. As will be appreciated by those skilled in the art, the control circuitry may include a variety of additional circuitry and components, such as logic circuitry and additional comparators.

The voltage suppressor 18 may be configured to suppress both positive and negative voltage spikes, or two voltage suppressors and sensing loads can be implemented. In one embodiment, a first combination of a voltage suppressor and sensing load is configured to detect and suppress positive transient voltage spikes, and a second combination of a voltage suppressor and sensing load is configured to detect and suppress negative transient voltage spikes. As recognized by those skilled in the art, the protection circuit is not limited to detection and suppression of pre-arcing and arcing conditions in a humidifier heater circuit, and the protection circuit may be used to detect and suppress pre-arcing and arcing conditions in a plurality of electrical applications.

Figure 2:
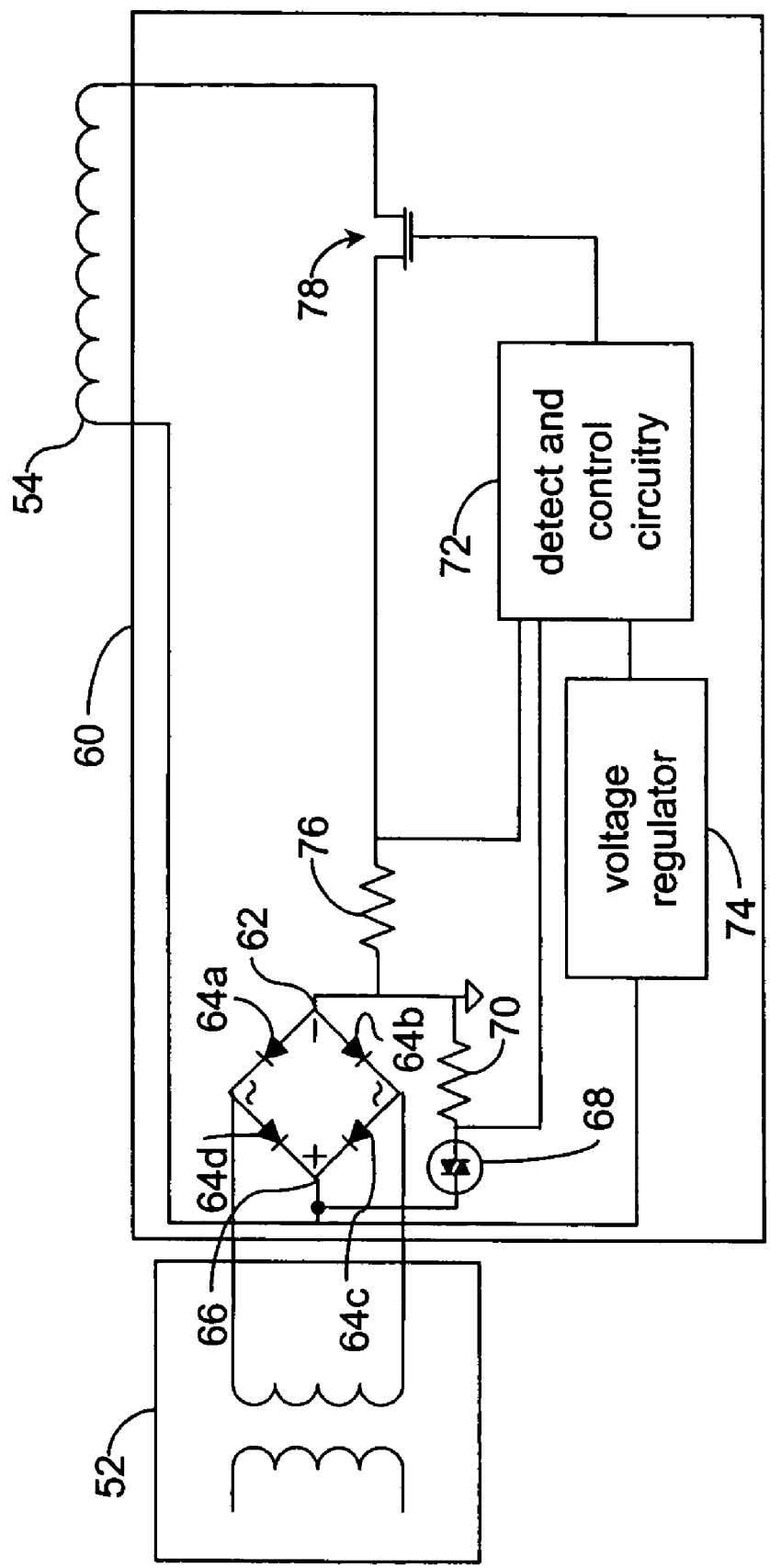
FIG. 2 is a block diagram of another embodiment of a humidifier heater circuit including an electrical arcing protection circuit of the present invention.
Figure 3A:
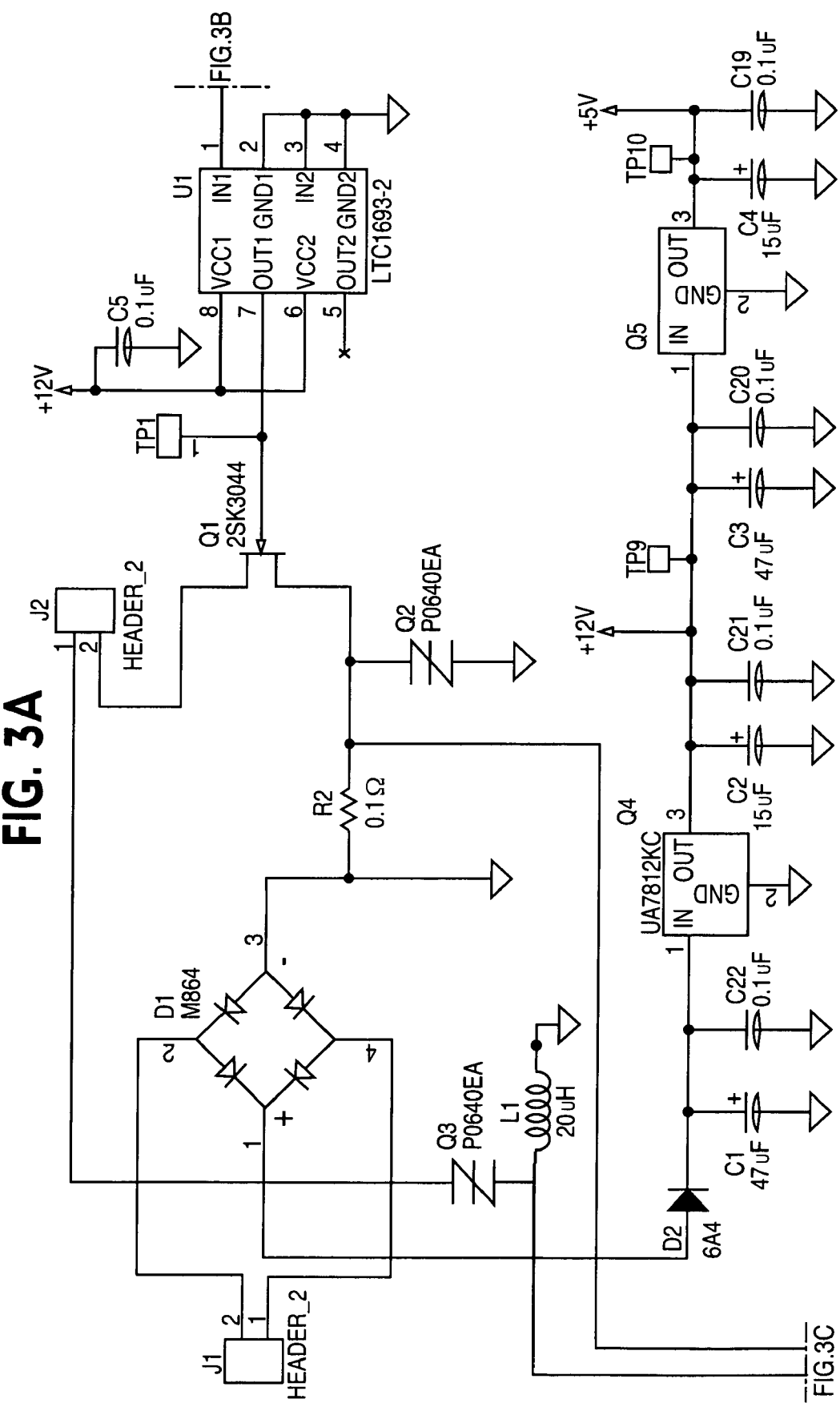
FIG. 3A, FIG. 3B, FIG. 3C, and FIG. 3D together comprise a schematic block diagram of one embodiment of the protection circuit of FIG. 2.
Figure 3B:
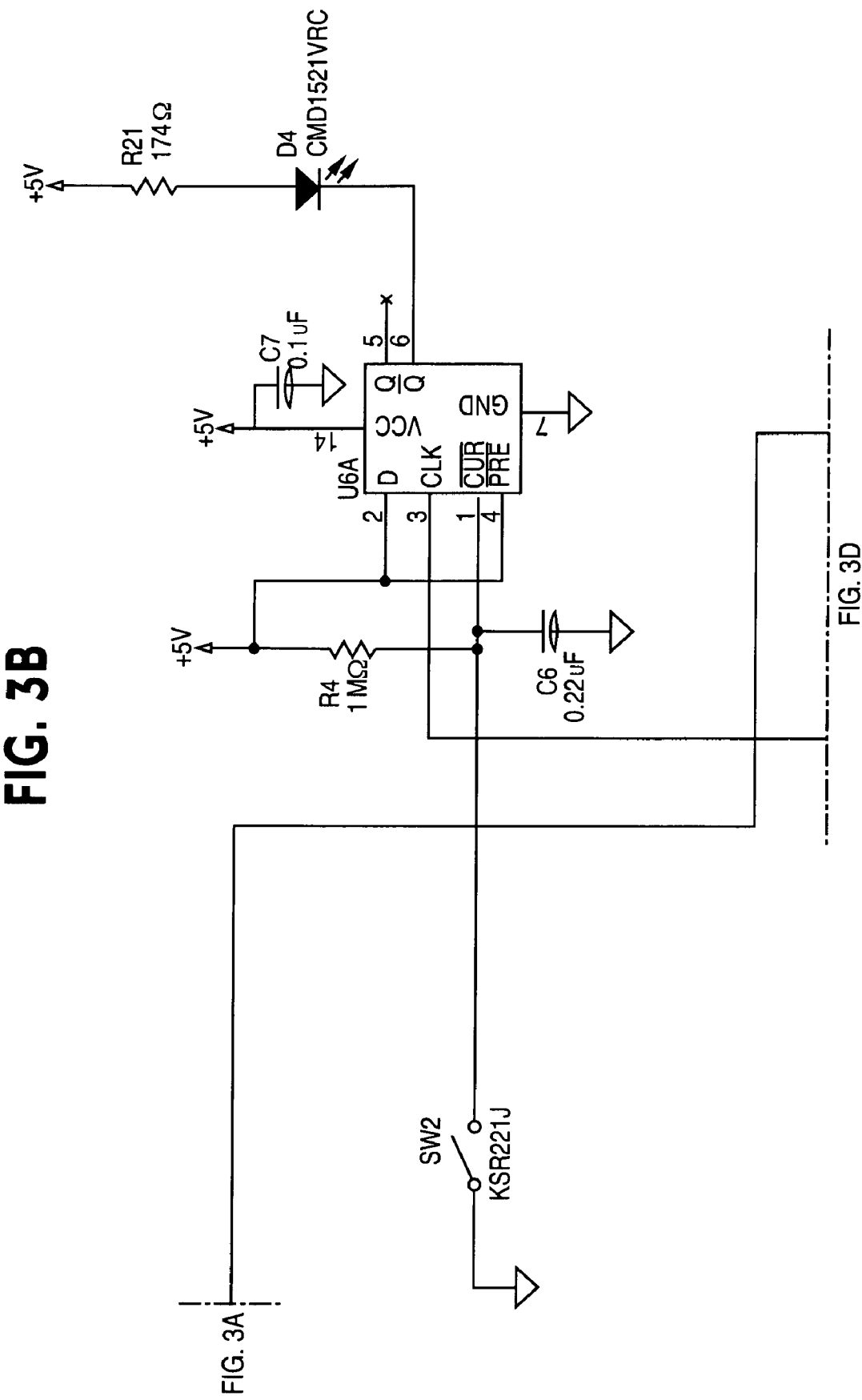
Figure 3C:
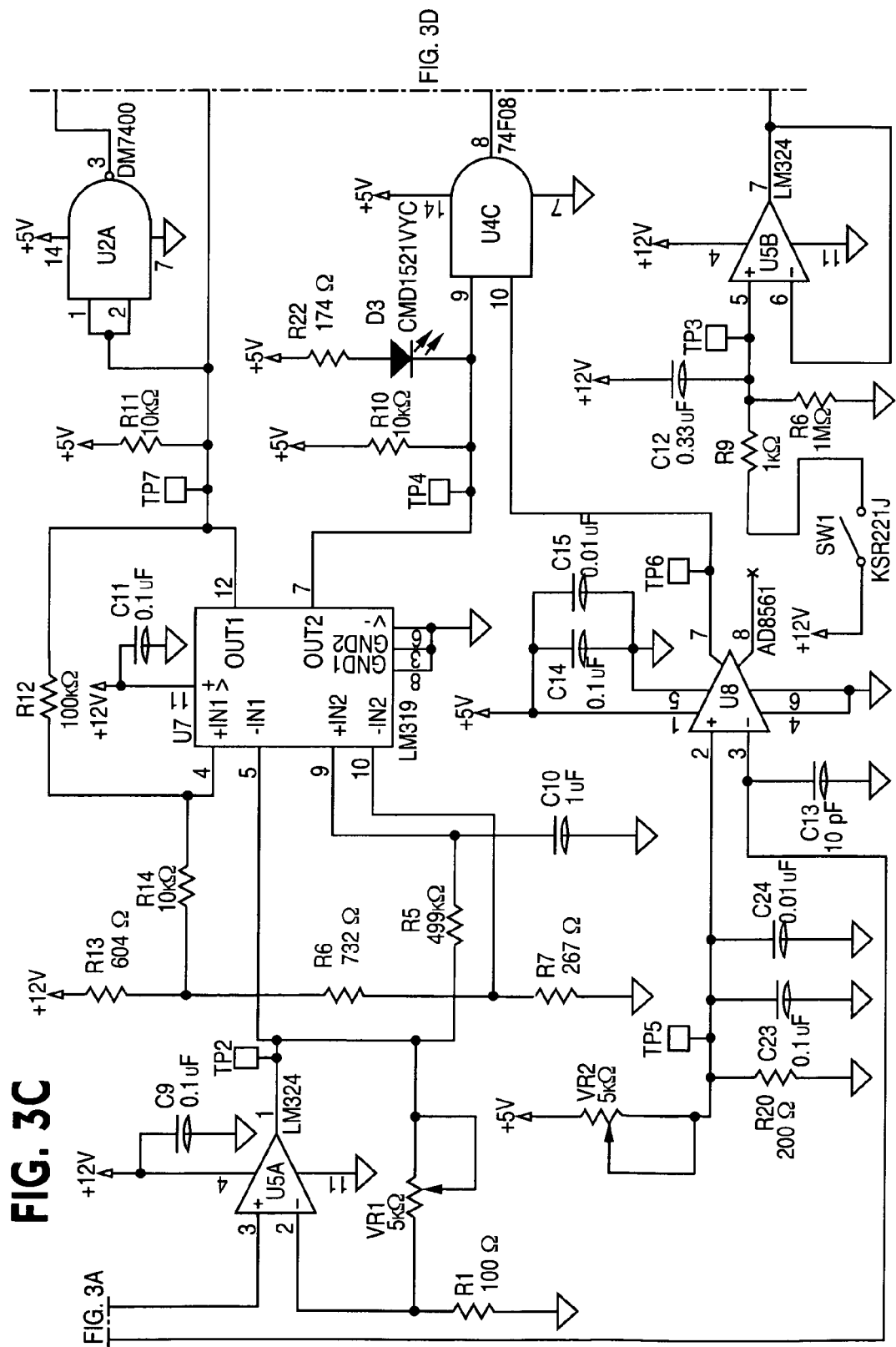
Figure 3D:
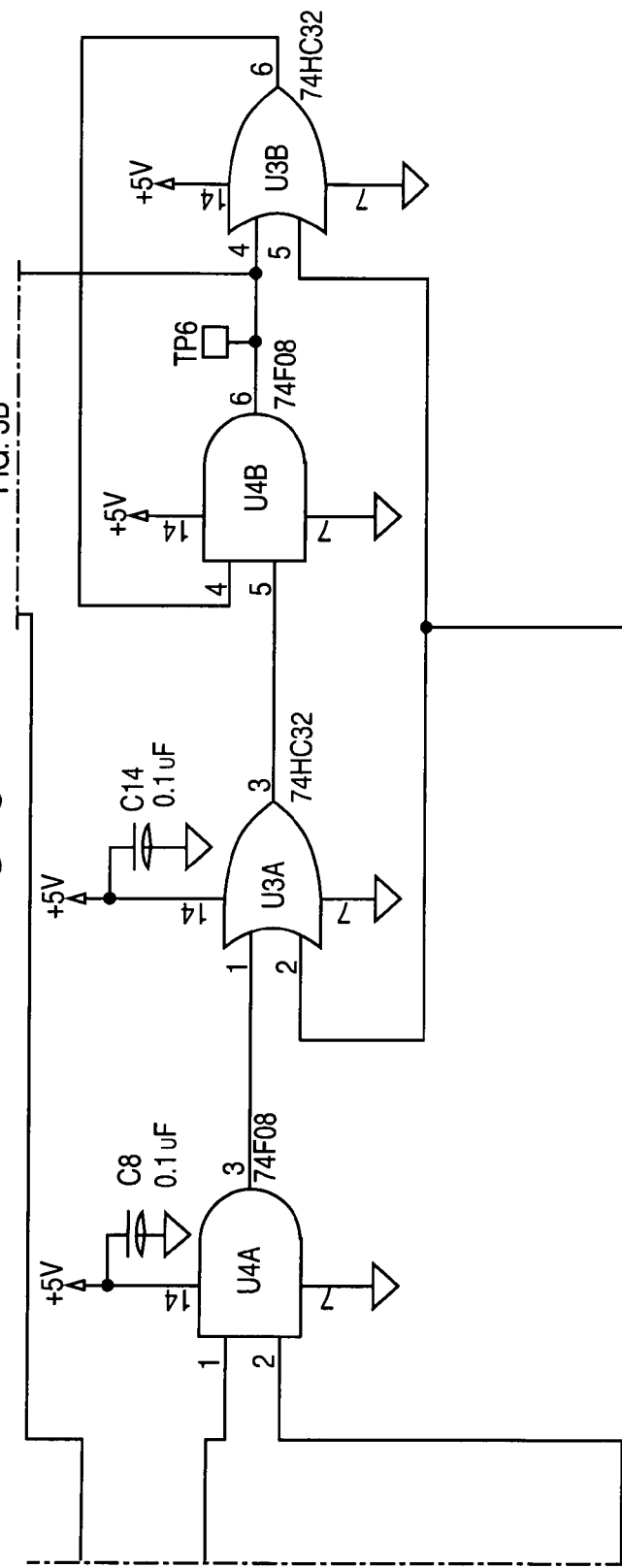
Figure 3D:
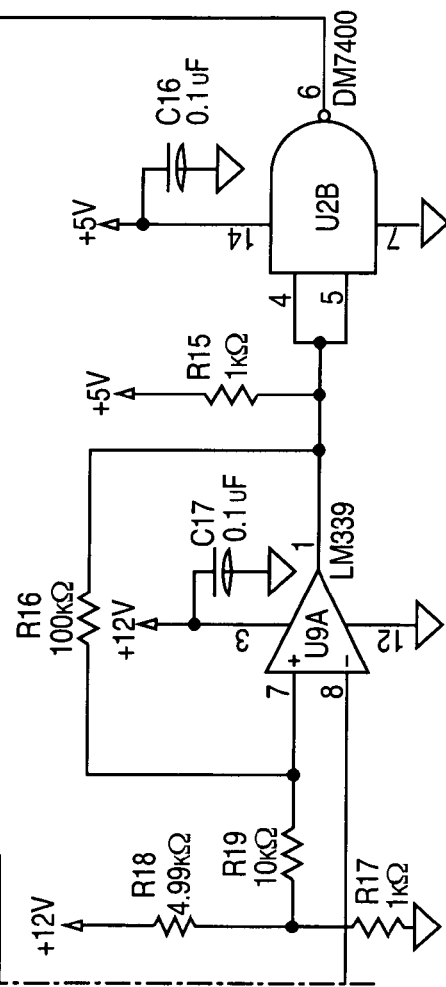

FIG. 2 illustrates one embodiment of an electrical arcing protection circuit 60, coupled between a voltage supply transformer 52 and a heater wire 54. In response to detection of an arcing or pre-arcing condition, the protection circuit 60 is configured to terminate the voltage supplied to the heater wire 54 and dissipate energy stored in the heater wire 54.

In the embodiment shown in FIG. 2, the protection circuit 60 comprises a voltage rectifier 62 coupled to a secondary winding of the transformer 52. The signal rectification allows the protection circuit 60 to detect positive spikes in current rather than monitor both the positive and negative aspects of the supply voltage waveform. As illustrated in FIG. 2, the voltage rectifier 62 is implemented with a bridge rectifier comprising four diodes 64A–D. Power dissipation by the diodes 64A–D result in a small power loss as provided to the heater wire 54, thereby allowing the protection circuit 60 to be self-powered.

A positive output 66 of the voltage rectifier 62 is coupled to a voltage suppressor 68, and the output of the voltage suppressor 68 is coupled to a first level sensing load in the form of a resistor 70 and control circuitry 72. As will be appreciated by those skilled in the art, the first sensing load 70 may be implemented with a component or combination of components other than a resistor, such as an inductor. The sensing resistor 70 is coupled to ground such that when transient voltage spikes at the voltage suppressor 68 exceed a predefined threshold, the voltage suppressor 68 sinks current through the first sensing resistor 70. The positive output 66 of the voltage rectifier 62 is also coupled to a voltage regulator 74, which provides a regulated voltage supply to the control circuitry 72.

A negative output 67 of the voltage rectifier 62 is coupled to ground and a second sensing resistor 76, and the second sensing resistor 76 is coupled to the control circuitry and an N-channel MOSFET switch 78. The control circuitry 72 is also coupled to the switch 78, which is coupled to the hater wire 54, such that the control circuitry 72 operates the switch 78 to turn off the current supply to the heater wire 54 in response to detection of an arcing or pre-arcing condition. As will be appreciated by those skilled in the art, the control circuitry 72 advantageously includes logic circuitry, amplifiers, comparators, and additional components so as to output the desired signal to the MOSFET switch 78.

Short Circuit Protection

The second sensing resistor 76 is used to obtain a voltage level corresponding to the instantaneous current in the heater wire 54. The voltage level across the second sensing resistor 76 is supplied to a comparator in the control circuitry 72. In certain embodiments, an amplifier (U5A), as shown in FIG. 3, is coupled between the second sensing resistor 76 and a comparator (U7) and is configured to amplify the voltage provided to the comparator from the second sensing resistor 76. The comparator also receives a known threshold voltage and compares the voltage level across the second sensing resistor 76 to the threshold voltage. When the current in the heater wire exceeds a predefined threshold, thereby causing the voltage level across the second sensing resistor 76 to exceed the threshold voltage received at the comparator, the comparator outputs an appropriate signal to the MOSFET switch 78. In response to the signal from the comparator, the MOSFET switch 78 rapidly shuts off the current supply to the heater wire 54.

Open Circuit Protection

As discussed above, the voltage suppressor 68 is activated in the presence of transient voltage spikes exceeding a predefined level, such as 50 V, and sinks current through the first sensing resistor 70. Similar to the short circuit protection, the first sensing resistor 70 is used to obtain a voltage level corresponding to the current level through the voltage suppressor 68. The voltage level on the first sensing resistor 70 is monitored by the comparator in the control circuitry such that when the voltage level exceeds a predefined threshold, the comparator outputs an appropriate signal to the MOSFET switch 78. In response to the signal from the comparator, the MOSFET switch rapidly shuts off the current supply to the heater wire 54.

In the embodiment illustrated in FIG. 2, the protection circuit 60 includes a reset switch which enables the heater circuit to return to normal operating conditions. Alternatively, two reset switches can be provided for resetting the protection circuit in response to detection of each a short circuit condition and an open circuit condition. The protection circuit 60 can also include visual indicators, such as different colored light emitting diodes (LED's) configured to activate upon detection of an arcing or pre-arcing condition, and thereby notify a user that the current supply to the heater wire 54 has been shut off. For example, a yellow LED can be illuminated upon detection of an open circuit condition and a red LED can be activated upon detection of a short circuit condition.

FIGS. 3A, 3B, 3C, and 3D together are a schematic diagram illustrating one embodiment of an implementation of the protection circuit of FIG. 2. Where circuit components illustrated in FIGS. 3A, 3B, 3C, and 3D are known to persons skilled in the art they will not be discussed in detail. Moreover, the implementation illustrated in FIGS. 3A, 3B, 3C, and 3D are exemplary in nature, and modified or alternative circuits understood by those skilled in the art are within the scope of the invention. As illustrated in FIGS. 3A, 3B, 3C, and 3D, the protection circuit includes reset switches SW1, SW2, a yellow LED indicator D3 configured to illuminate upon detection of an open circuit condition, and a red LED indicator D4 configured to illuminate upon detection of a short circuit condition. Also included in the protection circuit of FIG. 3 is a high-speed comparator U7, and a plurality of logic gates and amplifier circuits. The MOSFET switch is implemented with an NMOSFET Q1, wherein the gate voltage at the MOSFET Q1 is dropped below an operational level through a latch U1 upon detection of an open or short circuit condition. Thereby, the current supply to the heater wire through header J2 is shut off upon detection of a pre-arcing or arcing condition.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

The invention claimed is:

1. An electrical arcing protection circuit, configured to detect and suppress electrical pre-arcing and arcing conditions in a resistive heater wire circuit, wherein the heater wire is coupled to a voltage source, comprising:
   a voltage suppressor, coupled to the voltage source and configured to detect and suppress transient voltage spikes in a voltage signal supplied by the voltage source;
   a first sensing load, coupled to the voltage suppressor;
   detection and control circuitry, coupled to the sensing load and configured to determine whether a voltage level at the first sensing load exceeds a first predefined voltage level; and
   a switch, coupled to the control circuitry and the heater wire, wherein said detection and control circuitry is configured to open the switch upon determining that the voltage level at the first sensing load exceeds the first predefined voltage level; and
   a second sensing load coupled to the voltage source and the detection and control circuitry.

2. The protection circuit of claim 1, wherein the detection and control circuitry is further configured to determine whether a voltage level at the second sensing load exceeds a second predefined voltage level, and to open the switch upon determining that the voltage level at the second sensing load exceeds the second predefined voltage level.

3. The protection circuit of claim 2, wherein the second sensing load is a resistor.

4. The protection circuit of claim 1, wherein the voltage suppressor is configured to suppress both positive and negative transient voltage spikes.

5. The protection circuit of claim 1, wherein the voltage suppressor is configured to dissipate excess current through the first sensing load in response to detection of a transient voltage spike or when the switch is opened.

6. The protection circuit of claim 1, wherein the switch is a MOSFET.

7. The protection circuit of claim 1, wherein the first sensing load is a resistor.

8. The protection circuit of claim 1, wherein the first sensing load is an inductor.

9. An electrical arcing protection circuit, configured to detect and suppress electrical pre-arcing and arcing conditions in a resistive heater wire circuit, wherein the heater wire is coupled to a voltage source, comprising:
   a voltage suppressor, coupled to the voltage source and configured to detect and suppress transient voltage spikes in a voltage signal supplied by the voltage source;
   a first sensing load, coupled to the voltage suppressor;
   detection and control circuitry, coupled to the sensing load and configured to determine whether a voltage level at the first sensing load exceeds a first predefined voltage level; and
   a switch, coupled to the control circuitry and the heater wire, wherein said detection and control circuitry is configured to open the switch upon determining that the voltage level at the first sensing load exceeds the first predefined voltage level, and wherein the switch is configured to open in less than 100 ns in response to a signal from the control circuitry.

10. A protection circuit, configured to detect electrical arcing conditions in a resistive heater wire circuit, comprising:
   a voltage rectifier coupled to a voltage source, said voltage rectifier comprising a first signal output and a second signal output, wherein the first signal output is coupled to ground and the second signal output is coupled to a first end of the heater wire;
   a first signal level sensing load, coupled to said first signal output of said voltage rectifier;
   a voltage suppressor, coupled to said second signal output of said voltage rectifier;
   a second signal level sensing load, coupled to said voltage suppressor;
   detection and control circuitry, comprising a first input coupled to the output of said first signal level sensing load, and a second input coupled between said voltage suppressor and said second signal level sensing load, wherein the control circuitry comprises at least one comparator; and
   a switch coupled between said detection and control circuitry and a second end of the heater wire, wherein the position of the switch is controlled by the detection and control circuitry such that the switch is opened in response to detection of an electrical pre-arcing or arcing condition.

11. The protection circuit of claim 10, wherein the voltage rectifier is a full-wave bridge rectifier.

12. The protection circuit of claim 10, wherein the first signal level sensing load is a resistor.

13. The protection circuit of claim 10, wherein the second signal level sensing load is a resistor.

14. The protection circuit of claim 10, wherein the first signal level sensing load is an inductor.

15. The protection circuit of claim 10, wherein the second signal level sensing load is an inductor.

16. The protection circuit of claim 10, wherein the switch is a MOSFET.

17. The protection circuit of claim 10, further comprising a voltage regulator coupled between said second signal output of said voltage rectifier and said detection and control circuitry and configured to provide a regulated voltage signal to the detection and control circuitry.

18. The protection circuit of claim 10, wherein the voltage suppressor is configured to dissipate excess energy stored in the heater wire in response to detection of an electrical pre-arcing or arcing condition.

19. A respiratory breathing circuit comprising one or more limbs of hollow gas delivery tubing having a heater wire extending interiorly therein along a substantial portion of the length of one or more limbs of said hollow tubing, and
   an arc suppression and arc detection circuit cooperating with said heater wire comprising:
   a voltage suppressor, coupled to a voltage source and configured to detect and suppress transient voltage spikes in a voltage signal supplied by the voltage source;
   a first sensing load, coupled to the voltage suppressor;
   detection and control circuitry, coupled to the first sensing load and configured to determine whether a voltage level at the first sensing load exceeds a first predefined voltage level; and
   a switch, coupled to the detection and control circuitry and the heater wire, wherein said detection and control circuitry is configured to open the switch upon determining that the voltage level at the first sensing load exceeds the first predefined voltage levels,
   wherein the arc suppression and arc detection circuit further comprises a second sensing load coupled to the voltage source and the detection and control circuitry, wherein the detection and control circuitry is further configured to determine whether a voltage level at the second sensing load exceeds a second predefined voltage level, and to open the switch upon determining that the voltage level at the second sensing load exceeds the second predefined voltage level.

20. The respiratory breathing circuit of claim 19, wherein the second sensing load is a resistor.

21. The respiratory breathing circuit of claim 19, wherein the second sensing load is an inductor.

22. The respiratory breathing circuit of claim 19, wherein the voltage suppressor is configured to suppress both positive and negative transient voltage spikes.

23. The respiratory breathing circuit of claim 19, wherein the voltage suppressor is configured to dissipate excess current through the first sensing load in response to detection of a transient voltage spike or when the switch is opened.

24. The respiratory breathing circuit of claim 19, wherein the switch is a MOSFET.

25. The respiratory breathing circuit of claim 19, further comprising a voltage rectifier coupled to the voltage source, comprising a first signal output and a second signal output, wherein the first signal output is coupled to the second sensing load and ground, and the second signal output is coupled to a first end of the heater wire and the voltage suppressor, and wherein the control circuitry is coupled to the second sensing load and configured to open the switch in response to detecting the voltage at the second sensing load above a second predefined voltage threshold.

26. The respiratory breathing circuit of claim 25, wherein the voltage rectifier is a full-wave bridge rectifier.

27. The respiratory breathing circuit of claim 19, wherein the signal level sensing load is a resistor.

28. The respiratory breathing circuit of claim 19, wherein the first sensing load is a resistor.

29. The respiratory breathing circuit of claim 19, wherein the first sensing load is an inductor.

30. A respiratory breathing circuit comprising one or more limbs of hollow gas delivery tubing having a heater wire extending interiorly therein along a substantial portion of the length of one or more limbs of said hollow tubing, and
  an arc suppression and arc detection circuit cooperating with said heater wire comprising:
  a voltage suppressor, coupled to a voltage source and configured to detect and suppress transient voltage spikes in a voltage signal supplied by the voltage source;
  a first sensing load, coupled to the voltage suppressor;
  detection and control circuitry, coupled to the first sensing load and configured to determine whether a voltage level at the first sensing load exceeds a first predefined voltage level; and
  a switch, coupled to the detection and control circuitry and the heater wire, wherein said detection and control circuitry is configured to open the switch upon determining that the voltage level at the first sensing load exceeds the first predefined voltage level, and wherein the switch is configured to open in less than 100 ns in response to a signal from the control circuitry.

31. A method of detecting arcing conditions in a resistive heater wire circuit, comprising:
  suppressing a voltage level of a rectified power signal in response to the voltage level of said rectified power signal exceeding a predefined threshold, thereby providing a suppressed voltage signal;
  sensing a first current level of said suppressed voltage signal at a first sensing load;
  sensing a second current level at a second sensing load;
  comparing said first sensed current level to a first threshold level;
  comparing said second sensed current level to a second threshold level;
  stopping the supply of current to the heater wire in response to detection of said first sensed current level exceeding said first threshold level; and
  stopping the supply of current to the heater wire in response to detection of said second sensed current level exceeding said second threshold level.

32. The method of claim 31, wherein sensing said current level comprises generating a voltage signal having a value corresponding to the current level supplied to the heater wire.

33. The method of claim 31, further comprising rectifying the input power signal to provide a rectified power signal, prior to suppressing a voltage level of the input power signal.

34. A method of detecting arcing conditions in a resistive heater wire circuit, comprising:
  suppressing transient voltage spikes detected in a power signal supplied to the heater wire in response to the voltage level of the power signal exceeding a predefined threshold;
  sinking excess current through a first load;
  sensing a first current level in said first load;
  comparing said first sensed current level to a first predefined threshold;
  stopping the supply of current to the heater wire in response to detection of said first sensed current level exceeding said first predefined threshold;
  sinking excess current through a second load;
  sensing a second current level in said second load;
  comparing said second sensed current level to a second predetermined threshold; and
  stopping the supply of current to the heater wire in response to detection of said second sensed current level exceeding said second predefined threshold.

35. The method of claim 34, wherein sensing said current level comprises generating a voltage signal having a value corresponding to the current level supplied to the heater wire.

* * * * *